US006566115B1

(12) United States Patent
Weisgerber et al.

(10) Patent No.: US 6,566,115 B1
(45) Date of Patent: May 20, 2003

(54) PROTEASE CONJUGATES HAVING STERICALLY PROTECTED CLIP SITES

(75) Inventors: David John Weisgerber, Cincinnati, OH (US); Donn Nelton Rubingh, Cincinnati, OH (US); Paul Elliott Correa, Cincinnati, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

(21) Appl. No.: 09/618,740

(22) Filed: Jul. 18, 2000

Related U.S. Application Data

(60) Provisional application No. 60/144,981, filed on Jul. 22, 1999.

(51) Int. Cl.⁷ .............................. C12N 9/54; C12N 9/55; C12N 15/57; C12N 15/74; C11D 3/386
(52) U.S. Cl. ...................... 435/221; 435/69.1; 435/222; 435/252.3; 435/320.1; 435/471; 510/350; 524/267; 536/23.2
(58) Field of Search .................... 435/221, 222, 435/69.1, 471, 252.31, 320.1; 510/350; 524/267; 536/23.2

(56) References Cited

U.S. PATENT DOCUMENTS

| | | | |
|---|---|---|---|
| 4,179,337 A | 12/1979 | Davis et al. ................. | 435/181 |
| 4,248,786 A | 2/1981 | Batz .......................... | 260/326 |
| 4,266,031 A | 5/1981 | Tang et al. .................. | 435/188 |
| 4,556,554 A | 12/1985 | Calvo ......................... | 424/70 |
| 4,732,863 A | 3/1988 | Tomasi et al. ............... | 436/547 |
| 4,760,025 A | 7/1988 | Estell ........................ | 435/222 |
| 4,980,288 A | 12/1990 | Bryan ........................ | 435/222 |
| 5,122,614 A | 6/1992 | Zalipsky ..................... | 548/520 |
| 5,133,968 A | 7/1992 | Nakayama ................... | 424/401 |
| 5,208,158 A | 5/1993 | Bech et al. .................. | 435/219 |
| 5,230,891 A | 7/1993 | Nakayama ................... | 424/401 |
| 5,324,844 A | 6/1994 | Zalipsky ..................... | 548/520 |
| 5,352,603 A | * 10/1994 | Vetter et al. ................. | 435/221 |
| 5,414,135 A | 5/1995 | Snow et al. .................. | 568/29 |
| 5,446,090 A | 8/1995 | Harris ........................ | 525/54 |
| 5,543,302 A | 8/1996 | Boguslawski et al. | |
| 5,631,322 A | 5/1997 | Veronese et al. .......... | 525/54.1 |
| 5,658,871 A | 8/1997 | Battenburg et al. .... | 252/174.12 |
| 5,766,897 A | * 6/1998 | Braxton ...................... | 435/471 |
| 5,766,898 A | 6/1998 | Loevburg | |
| 5,856,451 A | 1/1999 | Olsen et al. ................. | 530/402 |
| 5,972,339 A | 10/1999 | Walker | |
| 5,985,264 A | 11/1999 | Metzger et al. | |
| 5,985,639 A | * 11/1999 | Christianson et al. ....... | 435/221 |
| 6,060,546 A | * 5/2000 | Powell et al. ............... | 524/267 |
| 6,300,116 B1 | * 10/2001 | van der Osten et al. .... | 435/220 |
| 6,312,936 B1 | * 11/2001 | Poulouse et al. ........... | 435/219 |

FOREIGN PATENT DOCUMENTS

| | | |
|---|---|---|
| DE | 2 206 826 | 8/1973 |
| EP | 0 130 756 | 1/1985 |
| EP | 1 215 662 | 3/1987 |
| EP | 0 260 105 | 3/1988 |
| EP | 0 398 539 | 11/1990 |
| EP | 0 405 901 | 1/1991 |
| EP | 0 471 125 | 12/1992 |
| EP | 0 516 2000 | 12/1992 |
| EP | 0 584 876 | 3/1994 |
| EP | 0 251 446 | 12/1994 |
| EP | 0 816 381 | 1/1998 |
| WO | WO 87/04461 | 7/1987 |
| WO | WO87/05050 | 8/1987 |
| WO | WO88/07578 | 10/1988 |
| WO | WO88/08028 | 10/1988 |
| WO | WO 88/08033 | 10/1988 |
| WO | WO88/08164 | 10/1988 |
| WO | WO 88/08165 | 10/1988 |
| WO | WO 92/10755 | 6/1992 |
| WO | WO 93/15189 | 8/1993 |
| WO | WO 93/19731 | 10/1993 |
| WO | WO 93/19732 | 10/1993 |
| WO | WO93/25667 | 12/1993 |
| WO | WO 94/04193 | 3/1994 |
| WO | WO95/07991 | 3/1995 |
| WO | WO 95/101615 | 4/1995 |
| WO | WO95/20039 | 7/1995 |
| WO | WO 95/29979 | 11/1995 |
| WO | WO 95/30010 | 11/1995 |
| WO | WO 96/09396 | 3/1996 |
| WO | WO 96/16177 | 5/1996 |
| WO | WO 96/17929 | 6/1996 |
| WO | WO 96/40791 | 12/1996 |
| WO | WO 96/40792 | 12/1996 |
| WO | WO 97/07770 | 3/1997 |
| WO | WO 97/24421 | 7/1997 |
| WO | WO 97/24427 | 7/1997 |
| WO | WO 97/30148 | 8/1997 |
| WO | WO 97/37007 | 10/1997 |

(List continued on next page.)

OTHER PUBLICATIONS

Davis, F. F., et al., 1990, "Reduction of immunogenicity and extension of circulating half–life of peptides and proteins", Advances in Parenteral Science, vol. 4, pp. 831–864.*

(List continued on next page.)

Primary Examiner—Ponnathapu Achutamurthy
Assistant Examiner—William W. Moore
(74) Attorney, Agent, or Firm—Dara M. Kendall; Brent M. Peebles; Tara M. Rosnell

(57) ABSTRACT

The present disclosure relates to subtilisin protease conjugate comprising a protease moiety and one or more addition moieties. Each addition moiety is covalently attached to a clip site protection position of the protease moiety, wherein the clip site protection positions are selected from 13, 14, 15, 16, 18, 19, 20, 21, 84, 85, 88, 158, 159, 160, 161, 162, 163, 164, 165, 170, 186, 191, 192, 193, 194, 196, 259, 260, 261, 262, and 274 corresponding to subtilisin BPN'. The protease conjugates have decreased immunogenicity relative to a parent protease. The present disclosure further relates to cleaning and personal care compositions comprising the protease conjugates.

19 Claims, No Drawings

U.S. PATENT DOCUMENTS

| WO | WO 98/23732 | 6/1998 |
|---|---|---|
| WO | WO 98/30682 | 7/1998 |
| WO | WO 98/35026 | 8/1998 |
| WO | WO 99/00489 | 1/1999 |
| WO | WO99/33868 | 7/1999 |
| WO | WO 99/37324 | 7/1999 |
| WO | WO99/40936 | 8/1999 |
| WO | WO99/41369 | 8/1999 |
| WO | WO99/42097 | 8/1999 |
| WO | WO99/44635 | 9/1999 |
| WO | WO99/45904 | 9/1999 |
| WO | WO 99/48918 | 9/1999 |
| WO | WO 99/49056 | 9/1999 |
| WO | WO00/9707 | 2/2000 |
| WO | WO 00/28007 | 5/2000 |
| WO | WO 00/37658 | 6/2000 |

OTHER PUBLICATIONS

Abuchowski, A., et al., 1981, "Soluble polymer–enzyme adducts", in Enzymes Drugs, Rutgers University Press, New Brunswick, New Jersey, Chapter 13, pp. 367–383.*

Masunaga, T., et al., 1993, "The protease as a cleansing agent and its stabilization by chemical modification", Journal of the Japanese Society of Cosmetic Chemsitry, vol. 27, pp. 276–288.*

Atassi, M.Z., et al., "Structure, Activity, and Immune (T and B Cell) Recognition of Botulinum Neurotoxins", Critical Reviews in Immunology, vol. 19, pp. 219–260 (1999).

Blaser, K., "Allergen Dose Dependent Cytokine Production Regulates Specific IgE and IgG Antibody Production", New Horizons in Allergy Immunotherapy, Sehon et al. (Ed.) Plenum Press, N.Y. (1996).

Cui, J., et al., "Inhibition of T Helper Cell Type 2 Cell Differentiation and Immunoglobulin E Response by Ligand–activated Vα14 Natural Killer T Cells", J. Exp. Med., vol. 190, No. 6, pp. 783–792, (Sep. 20, 1999).

Deml, L., et al., "Immunostimulatory CpG Motifs Trigger a T Helper–1 Immune Response to Human Immunodeficiency Virus Type–1 (HIV–1) gp 160 Envelope Proteins", Clin Chem Lab Med, vol. 37, No. 3, pp. 199–204 (1999).

Ferru, I., et al., "Comparison of the Immune Response Elicited by a Free Peptide and a Lipopeptide Construct", Peptide Research, vol. 9, No. 3, pp. 136–143 (1996).

Haack, T., et al., "D–Amino Acids in Protein De Novo Design. II. Protein–diastereomerism Versus Protein–enantiomerism", Letters in Peptide Science, vol. 4, pp. 377–386 (1997).

Herve, M., et al., "On the Immunogenic Properties of Retro–Inverso Peptides. Total Retro–Inversion of T–Cell Epitopes Causes a Loss of Binding to MHC II Molecules", Molecular Immunology, vol. 34, No. 2, pp. 157–163 (1997).

Hoyne, G. F., et al., "Peptide–Mediated Regulation of the Allergic Immune Response", Immunology and Cell Biology, vol. 74, pp. 180–186 (1996).

Ikagawa, S., MD., et al., "Single Amino Acid Substitutions on a Japanese Cedar Pollen Alleren (Cry j 1)–derived Peptide Induced Alterations in Human T Cell Responses and T Cell Receptor Antagonism", J. Allergy Clin. Immuno, vol. 97, No. 1, Part 1, pp. 53–64 (Jan. 1996).

Lofthouse, S. A., et al., "Induction of $T_2$ (cytotoxic lymphocyte) and/or $T_1$ (antibody) Responses to a Mucin–1 tumour Antigen", Vaccine, vol. 15, No. 14, pp. 1586–1593 (1997).

Maillere, B., et al., "Probing Immunogenicity of a T–Cell Epitope by L–Alanine and D–Amino Acid Scanning", Molecular Immunology, vol. 32, No. 14/15, pp. 1073–1080 (1995).

McKee, H. J., et al., "T Cell Cytokine Responses to Cartilage Aggrecan in BALB/c Mice", Biochemical Society Transactions, vol. 25, p 311S (1997).

Moore, A., et al., "The Adjuvant Combination Monophosphoryl Lipid A and QS21 Switches T Cell Responses Induced With a Soluble Recombinant HIV Protein from Th2 and Th1", Vaccine, vol. 17, pp. 2517–2527 (1999).

Rosenthal, K. S., et al., "Immunization with a LEAPS™ Heteroconjugate Containing a CTL Epitope and a Peptide from Beta–2–microglobulin Elicits a Protective and DTH Response to Herpes Simplex Virus Type 1", Vaccine, vol. 17, pp. 535–542 (1999).

Sinha, P., et al., "A Minimized Fc Binding Peptide from Protein A Induces Immunocyte Proliferation and Evokes Th1–Type Response in Mice", Biochemical and Biophysical Research Communications, vol. 258, pp. 141–147 (1999).

Specht, C., et al., "The Murine ($H-2^K$) T–Cell Epitopes of Bee Venom Phospholipase $A_2$ Lie Outside the Active Site of the Enzyme", Int Arch Allergy Immunol, vol. 112, pp. 226–230 (1997).

Wiedermann, U., et al., "Effects of Adjuvants on the Immune Response to Allergens in a Murine Model of Allergen Inhalation: Cholera Toxin Induces a Th1–like Response to Bet V 1, the Major Birch Pollen Allergen", Clin Exp Immunol, vol. 111, pp. 144–151 (1998).

Zimmerman, D. H., et al., "Immunization with Peptide Heteroconjugates Primes a T Helper Cell Type 1–Associated Antibody (IgG2a) Response that Recognizes the Native Epitope on the 38–kDa Protein of *Mycobacterium tuberculosis*", Vaccine Research, vol. 5, No. 2, pp. 103–118 (1996).

Gundlach, B.R., et al., "Determination of T Cell Epitopes with Random Peptide Libraries", Journal of Immunological Methods, vol. 192, pp. 149–155 (1996).

Siezen, R.J., et al., "Subtilases: The Superfamily of Subtilisin–like Serine Proteases", Protein Science, vol. 6, No. 3, pp 501–523 (1997).

Yang, M–L., et al., "Chemical Modification of Cobrotoxin with Bifunctional Reagent, 1,5–Difluoro–2,4–Dinitrobenzene", Kaohsiung J. Med. Sci., vol. 4, pp 503–513 (1988).

Mitchinson, C., et al., "Protein Engineering of Disulfide Bonds in Subtilisin BPN", Biochemistry, vol. 28, No. 11, pp. 4807–4815 (1989).

Nucci, M. L., et al., "Immunogenicity of Polyethylene Glycol–Modified Superoxide Dismutase and Catalase", J. Free Radicals in Biology & Medicine, vol. 2, pp. 321–325 (1986).

Arlian, L.G. et al., "Antigenic and Allergenic Characteristics of the Enzyms Alcalase and Savinase by Crossed Immunoelectrophoresis and Crossed Radioimmunoelectrophoresis", Int. Arch Allergy Appl Immunol, vol. 91, pp. 278–284 (1990).

Abuchowski, A. et al., "Cancer Therapy with Chemically Modified Enzymes. I. Antitumor Properties of Polyethylene Glycol–Asparaginase Conjugates", Cancer Biochem Biophys, vol. 7, pp. 175–186 (1984).

Bungy Poor Fard, G.A. et al., T Cell Epitopes of the Major Fraction of Rye Grass Lolium Perenne (IoI p I) Defined Using Overlapping Peptides in Vitro and In Vivo. I. Isoallergen Clone 1A, Clin Exp Immunol, vol. 94, pp. 111–116 (1993).

Caliceti, P. et al., "Active Site Protection of Proteolytic Enzymes by Poly(ethylene glycol) Surface Modification" Journal of Bioactive and Compatible Polymers, vol. 8, Jan., 1993, pp. 41–50.

Delgado, C. et al., "The Uses and Properties of PEG–Linked Proteins", Critical Review in Therapeutic Drug Carrier Systems, 9(3,4) (1992), pp. 249–304.

Favre, C. et al., "Epitope Mapping of Recombinant Human Gamma Interferon Using Monoclonal Antibodies", Molecular Immunology, vol. 26, No. 1, pp. 17–25 (1989).

Francis, G.E. et al., "PEG–Modified Proteins", Stability of Protein Pharmaceuticals, Part B: In Vivo Pathways of Degradation and Strategies for Protein Stabilization, edited by Ahern, T.J. and Mannin, M.C., Plenum Press (1992), pp. 235–263.

Hopp, T.P. et al., "Prediction of Protein Antigenic Determinants from Amino Acid Sequences", Proc. Natl. Acad Sci, vol. 78, No. 6, pp. 3824–3828 (1981).

Katre, N.V., "The Conjugation of Proteins with Polyethylene Glycol and Other Polymers", Advanced Drug Delivery Reviews, 10 (1993), pp. 92–114.

Khan, S.A. et al., "Polyethylene Glycol–modified Subtilisin Forms Microparticulate Suspensions in Organice Solvents", Enzyme Microb. Technology, vol. 14, Feb. (1992), pp. 96–100.

Masakatsu Ohta et al., "Preparation of a Dextran–Protease Conjugate and its Application to Cosmetic Use", 1996, Kanebo, Ltd., Cosmetics Laboratory, Japan, Cosmetics and Toiletries, vol. 111, pp. 79–88.

Monfardini, C. et al., "A Branched Monoethoxy Poly(ethylene glycol) for Protein Modification", Biconjugate Chemistry, vol. 6, No. 1 (1995), pp. 62–69.

Nishimura, H. et al., "Improved Modification of Yeast Uricase with Polyethylene Glycol, Accompanied with Non-immunoreactivity Towards Anti–Uricase Serum and High Enzymic Activity", Enzyme 26 (1981), pp. 49–53.

Nucci, M.L. et al., "The Therapeutic Value of Poly(ethylene glycol)–modified Proteins", Advanced Drug Delivery Reviews, 6 (1991), pp. 133–149.

Reay, P.A. et al., "Use of Global Amino Acid Replacements to Define the Requirements for MHC Binding and T Cell Recognition of Moth Cytochrome c (93–103)", Journal of Immunology, vol. 152, No. 8, pp. 3946–3957 (1994).

Ritz, H.L. et al., "Respiratory and Immunological Responses of Guinea Pigs to Enzyme–Containing Detergents: A Comparison of Intratracheal and Inhalation Modes of Exposure", Fundamental and Applied Toxicology, vol. 21, pp. 31–37 (1993).

Robinson, M.K. et al., "Specific Antibody Responses to Subtilisin Carlsberg (Alcalase) in Mice: Development of an Intranasal Exposure Model", Fundamental and Applied Toxicology, vol. 24, pp. 15–24 (1996).

Savoca, K.V. et al., "Preparation of a Non–immunogenic Agrinase by the Covalent Attachment of Polyethylene Glycol", Biochemica et Biophysica Acta, 578 (1979), pp. 47–53.

Siezen et al., "Homology Modelling and Protein Engineering Strategy of Subtilases, the Family of Subtilisin–Like Serine Proteases", Protein Engineering, vol. 4, No. 7, pp. 719–737 (1991).

Walsh, B.J. and M.E.H. Howden, "A Method for the Detection of IgE Binding Sequences of Allergens Based on a Modification of Epitope Mapping", Journal of Immunological Methods, vol. 121, pp. 275–280 (1989).

* cited by examiner

SEQUENCE LISTING

<160> NUMBER OF SEQ ID NOS: 1

<210> SEQ ID NO 1
<211> LENGTH: 275
<212> TYPE: PRT
<213> ORGANISM: Bacillus amyloliquefaciens

<400> SEQUENCE: 1

```
Ala Gln Ser Val Pro Tyr Gly Val Ser Gln Ile Lys Ala Pro Ala Leu
 1               5                  10                  15

His Ser Gln Gly Tyr Thr Gly Ser Asn Val Lys Val Ala Val Ile Asp
            20                  25                  30

Ser Gly Ile Asp Ser Ser His Pro Asp Leu Lys Val Ala Gly Gly Ala
        35                  40                  45

Ser Met Val Pro Ser Glu Thr Asn Pro Phe Gln Asp Asn Asn Ser His
    50                  55                  60

Gly Thr His Val Ala Gly Thr Val Ala Ala Leu Asn Asn Ser Ile Gly
65                  70                  75                  80

Val Leu Gly Val Ala Pro Ser Ala Ser Leu Tyr Ala Val Lys Val Leu
```

-continued

```
                    85                      90                      95
Gly Ala Asp Gly Ser Gly Gln Tyr Ser Trp Ile Ile Asn Gly Ile Glu
            100                 105                 110

Trp Ala Ile Ala Asn Asn Met Asp Val Ile Asn Met Ser Leu Gly Gly
        115                 120                 125

Pro Ser Gly Ser Ala Ala Leu Lys Ala Ala Val Asp Lys Ala Val Ala
        130                 135                 140

Ser Gly Val Val Val Ala Ala Gly Asn Glu Gly Thr Ser Gly
145                 150                 155                 160

Ser Ser Ser Thr Val Gly Tyr Pro Gly Lys Tyr Pro Ser Val Ile Ala
            165                 170                 175

Val Gly Ala Val Asp Ser Ser Asn Gln Arg Ala Ser Phe Ser Ser Val
            180                 185                 190

Gly Pro Glu Leu Asp Val Met Ala Pro Gly Val Ser Ile Gln Ser Thr
        195                 200                 205

Leu Pro Gly Asn Lys Tyr Gly Ala Tyr Asn Gly Thr Ser Met Ala Ser
        210                 215                 220

Pro His Val Ala Gly Ala Ala Ala Leu Ile Leu Ser Lys His Pro Asn
225                 230                 235                 240

Trp Thr Asn Thr Gln Val Arg Ser Ser Leu Glu Asn Thr Thr Thr Lys
            245                 250                 255

Leu Gly Asp Ser Phe Tyr Tyr Gly Lys Gly Leu Ile Asn Val Gln Ala
            260                 265                 270

Ala Ala Gln
        275
```

PROTEASE CONJUGATES HAVING STERICALLY PROTECTED CLIP SITES

CROSS REFERENCE TO RELATED APPLICATION

This application claims the benefit of U.S. Provisional Application No. 60/144,981, filed Jul. 22, 1999.

FIELD OF THE INVENTION

The present invention relates to chemically modified subtilisin proteases which are useful in compositions such as, for example, personal care compositions, laundry compositions, hard surface cleansing compositions, and light duty cleaning compositions.

BACKGROUND OF THE INVENTION

Enzymes make up the largest class of naturally occurring proteins. One class of enzyme includes proteases which catalyze the hydrolysis of other proteins. This ability to hydrolyze proteins has typically been exploited by incorporating naturally occurring and genetically engineered proteases into cleaning compositions, particularly those relevant to laundry applications.

In the cleaning arts, the mostly widely utilized of these proteases are the serine proteases. Most of these serine proteases are produced by bacterial organisms while some are produced by other organisms, such as fungi. See Siezen et al., "Homology Modelling and Protein Engineering Strategy of Subtilases, the Family of Subtilisin-Like Serine Proteases", *Protein Engineering*, Vol. 4, No. 7, pp. 719–737 (1991). Unfortunately, the efficacy of the wild-type proteases in their natural environment is frequently not optimized for the artificial environment of a cleaning composition. Specifically, protease characteristics such as, for example, thermal stability, pH stability, oxidative stability, and substrate specificity are not necessarily optimized for utilization outside the natural environment of the protease.

Several approaches have been employed to alter the wild-type amino acid sequence of serine proteases with the goal of increasing the efficacy of the protease in the unnatural wash environment. These approaches include the genetic redesign and/or chemical modification of proteases to enhance thermal stability and to improve oxidation stability under quite diverse conditions.

However, because such modified proteases are foreign to mammals, they are potential antigens. As antigens, these proteases cause an immunogenic and/or allergenic response (herein collectively described as immunogenic response) in mammals.

Furthermore, while genetic redesign and chemical modification of proteases has been prominent in the continuing search for more highly effective proteases for laundry applications, such proteases have not been commercially utilized in personal care compositions and light duty detergents. A primary reason for the absence of these proteases in products such as, for example, soaps, gels, body washes, shampoos, and light duty dish detergents is due to the problem of human sensitization leading to undesirable immunogenic responses. It would therefore be highly advantageous to provide a personal care composition or a light duty detergent which provides the cleansing properties of proteases without the provocation of an immunogenic response.

Presently, immunogenic response to proteases may be minimized by immobilizing, granulating, coating, or dissolving chemically modified proteases to avoid their becoming airborne. These methods, while addressing consumer exposure to airborne proteases, still present the risks associated with extended tissue contact with the finished composition.

It has also been proposed that reduction in immunogenicity of a protease may be achieved by attaching polymers to the protease. See. e.g., U.S. Pat. No. 4,179,337, Davis et al., issued Dec. 18, 1979; U.S. Pat. No. 5,856,451, Olsen et al., assigned to Novo Nordisk, issued Jan. 5, 1999; WO 99/00489, Olsen et al., assigned to Novo Nordisk, published Jan. 7, 1999; WO 98/30682, Olsen et al., assigned to Novo Nordisk, published Jul. 16, 1998; and WO 98/35026, Von Der Osten et al., published Aug. 13, 1998. However, such proposals have not suggested the importance of attaching polymers to particular amino acid regions of the protease in order to most effectively decrease the immunogenic response.

It has recently been discovered that the subtilisin protease comprises three epitope regions and that conjugation of one or more polymers, polypeptides, or other groups should be attached at one or more of these regions to effect significant reduction in immunogenicity of the protease. See, e.g., U.S. patent application Ser. No. 09/088,912, Weisgerber et al., assigned to The Procter & Gamble Co., filed Jun. 2, 1998.

As an alternative to protection of the epitope regions of the subtilisin protease, the present inventors have discovered that steric protection of one or more "clip sites" (i.e., locations of the protease where hydrolysis occurs in vivo) of the protease may be utilized to prevent or impede presentation of an epitope and decrease the immunogenicity of the protease. Accordingly, the present inventors provide chemically modified subtilisins wherein the chemical modification is at a region in steric proximity to one or more of the clip sites. The present inventors have therefore discovered subtilisin proteases which evoke a decreased immunogenic response yet maintain their activity as an efficient and active protease. Accordingly, the present protease conjugates are suitable for use in several types of compositions including, but not limited to, laundry, dish, hard surface, skin care, hair care, beauty care, oral care, and contact lens compositions.

SUMMARY OF THE INVENTION

The present invention relates to protease conjugates comprising a protease moiety and one or more addition moieties wherein each addition moiety is covalently attached to an amino acid of the protease moiety at a position selected from the group consisting of 13, 14, 15, 16, 18, 19, 20, 21, 84, 85, 88, 158, 159, 160, 161, 162, 163, 164, 165, 170, 186, 191, 192, 193, 194, 196, 259, 260, 261, 262, and 274 corresponding to subtilisin BPN'; wherein the addition moieties each, independently, have the structure:

wherein X is selected from the group consisting of nil and a linking moiety; $R_1$ is selected from the group consisting of nil, a first polypeptide, and a first polymer; and $R_2$ is selected from the group consisting of nil, a second polypeptide, and a second polymer; wherein at least one of X, $R_1$, and $R_2$ is not nil.

The protease conjugates of the present invention have decreased immunogenicity relative to the parent protease.

Accordingly, such protease conjugates are suitable for use in several types of compositions including, but not limited to, laundry, dish, hard surface, skin care, hair care, beauty care, oral care, and contact lens compositions.

DETAILED DESCRIPTION OF THE INVENTION

The essential components of the present invention are herein described below. Also included are non-limiting descriptions of various optional and preferred components useful in embodiments of the present invention.

The present invention can comprise, consist of, or consist essentially of any of the required or optional components and/or limitations described herein.

All percentages and ratios are calculated by weight unless otherwise indicated. All percentages are calculated based on the total composition unless otherwise indicated.

All component or composition levels are in reference to the active level of that component or composition, and are exclusive of impurities, for example, residual solvents or by-products, which may be present in commercially available sources.

All documents referred to herein, including all patents, patent applications, and publications, are hereby incorporated by reference in their entirety.

Referred to herein are trade names for materials including, but not limited to, enzymes. The inventors herein do not intend to be limited by materials under a certain trade name. Equivalent materials (e.g., those obtained from a different source under a different name or catalog (reference) number) to those referenced by trade name may be substituted and utilized in the protease conjugates and compositions herein.

As used herein, abbreviations will be used to describe amino acids. Table I provides a list of abbreviations used herein:

TABLE I

| Amino Acid | Three-letter Abbreviation | One-letter Abbreviation |
|---|---|---|
| Alanine | Ala | A |
| Arginine | Arg | R |
| Asparagine | Asn | N |
| Aspartic Acid | Asp | D |
| Cysteine | Cys | C |
| Glutamine | Gln | Q |
| Glutamic Acid | Glu | E |
| Glycine | Gly | G |
| Histidine | His | H |
| Isoleucine | Ile | I |
| Leucine | Leu | L |
| Lysine | Lys | K |
| Methionine | Met | M |
| Phenylalanine | Phe | F |
| Proline | Pro | P |
| Serine | Ser | S |
| Threonine | Thr | T |
| Tryptophan | Trp | W |
| Tyrosine | Tyr | Y |
| Valine | Val | V |

Definitions

As used herein, the term "mutation" refers to an alteration in a gene sequence and/or an amino acid sequence produced by those gene sequences. Mutations include deletions, substitutions, and additions of amino acid residues to the wild-type protein sequence.

As used herein, the term "parent" refers to a protein (wild-type or variant) which is utilized for further modification to form a protease conjugate herein.

As used herein, the term "wild-type" refers to a protein, for example a protease or other enzyme, produced by a naturally-occurring organism.

As used herein, the term "variant" means a protein having an amino acid sequence which differs from that of the corresponding wild-type protein.

As used herein, all polymer molecular weights are expressed as weight average molecular weights.

As referred to herein, while the conjugates of the present invention are not limited to those comprising subtilisin BPN' and variants thereof, all amino acid numbering is with reference to the amino acid sequence for subtilisin BPN' which is represented by SEQ ID NO:1. The amino acid sequence for subtilisin BPN' is further described by Wells et al., *Nucleic Acids Research*, Vol. II, pp. 7911–7925 (1983).

Protease Conjugates of the Present Invention

The protease conjugates of the present invention are compounds which comprise a protease moiety and one or more addition moieties, wherein the protease moiety and the addition moieties are connected via covalent attachment (i.e., covalent bonding).

Protease Moieties

The protease moieties herein are subtilisin-like proteases, either wild-type or variants thereof. As used herein, the term "subtilisin-like protease" means a protease which has at least 50%, and preferably 80%, amino acid sequence identity with the sequences of subtilisin BPN'. Wild-type subtilisin-like proteases are produced by, for example, *Bacillus alcalophilus, Bacillus amyloliquefaciens, Bacillus amylosaccharicus, Bacillus licheniformis, Bacillus lentus,* and *Bacillus subtilis* microorganisms. A discussion relating to subtilisin-like serine proteases and their homologies may be found in Siezen et al., "Homology Modelling and Protein Engineering Strategy of Subtilases, the Family of Subtilisin-Like Serine Proteases", *Protein Engineering*, Vol. 4, No. 7, pp. 719–737 (1991).

Preferred protease moieties for use herein include, for example, those obtained from *Bacillus amyloliquefaciens, Bacillus licheniformis,* and *Bacillus subtilis,* subtilisin BPN, subtilisin BPN', subtilisin Carlsberg, subtilisin DY, subtilisin 309, proteinase K, and thermitase, including A/S Alcalase® (commercially available from Novo Industries, Copenhagen, Denmark), Esperase® (Novo Industries), Savinase® (Novo Industries), Maxatase® (commercially available from Genencor International Inc.), Maxacal® (Genencor International Inc.), Maxapem 15® (Genencor International Inc.), and variants of the foregoing. Especially preferred protease moieties for use herein include those obtained from *Bacillus amyloliquefaciens* and variants thereof. The most preferred protease moieties herein are subtilisin BPN' and variants thereof.

Especially preferred variants of subtilisin BPN', hereinafter referred to as "Protease A", for use herein are disclosed in U.S. Pat. No. 5,030,378, Venegas, issued Jul. 9, 1991, as characterized by the subtilisin BPN' amino acid sequence with the following mutations:

(a) Gly at position 166 is substituted with an amino acid residue selected from Asn, Ser,. Lys, Arg, His, Gln, Ala and Glu; Gly at position 169 is substituted with Ser; and Met at position 222 is substituted with an amino acid residue selected from Gln, Phe, His, Asn, Glu, Ala and Thr; or (b) Gly at position 160 is substituted with Ala, and Met at position 222 is substituted with Ala.

Additionally preferred variants of subtilisin BPN', hereinafter referred to as "Protease B", for use herein are disclosed in EP 251,446, assigned to Genencor International, Inc., published Jan. 7, 1988, as characterized by the wild-type subtilisin BPN' amino acid sequence with mutations at one or more of the following positions: Tyr21, Thr22, Ser24, Asp36, Ala45, Ala48, Ser49, Met50, His67, Ser87, Lys94, Val95, Gly97, Ser101, Gly102, Gly103, Ile107, Gly110, Met124, Gly127, Gly128, Pro129, Leu135, Lys170, Tyr171, Pro172, Asp197, Met199, Ser204, Lys213, Tyr214, Gly215, and Ser221; or two or more of the positions listed above combined with one or more mutations at positions selected from Asp32, Ser33, Tyr104, Ala152, Asn155, Glu156, Gly166, Gly169, Phe189, Tyr217, and Met222.

Other preferred subtilisin BPN' variants for use herein are hereinafter referred to as "Protease C", and are described in WO 95/10615, assigned to Genencor International Inc., published Apr. 20, 1995, as characterized by the wild-type subtilisin BPN' amino acid sequence with a mutation to position Asn76, in combination with mutations in one or more other positions selected from Asp99, Ser101, Gln103, Try104, Ser105, Ile107, Asn109, Asn123, Leu126, Gly127, Gly128, Leu135, Glu156, Gly166, Glu195, Asp197, Ser204, Gln206, Pro210, Ala216, Tyr217, Asn218, Met222, Ser260, Lys265, and Ala274.

Other preferred subtilisin BPN' variants for use herein, hereinafter referred to as "Protease D", are described in U.S. Pat. No. 4,760,025, Estell et al., issued Jul. 26, 1988, as characterized by the wild-type subtilisin BPN' amino acid sequence with mutations to one or more amino acid positions selected from the group consisting of Asp32, Ser33, His64, Try104, Asn155, Glu156, Gly166, Gly169, Phe189, Tyr217, and Met222.

The more preferred protease moieties herein are selected from the group consisting of Alcalase®, subtilisin BPN', Protease A, Protease B, Protease C, and Protease D, with Protease D being the most preferred.

Without intending to be limited by theory, the protease moieties herein have at least two initial "clip sites", or regions of the protease moiety which are particularly susceptible to in vivo hydrolysis. The region which is most susceptible to in vivo hydrolysis is at amino acid positions 160 through 165, inclusive, corresponding to subtilisin BPN'. Another region susceptible to in vivo hydrolysis is amino acid positions 19 and 20, corresponding to subtilisin BPN'. The present inventors have discovered that these clip sites are protected from hydrolysis, and thus exposure of epitopes, by covalently attaching one or more addition moieties to an amino acid of the protease moiety at a position selected from 13, 14, 15, 16, 18, 19, 20, 21, 84, 85, 88, 158, 159, 160, 161, 162, 163, 164, 165, 170, 186, 191, 192, 193, 194, 196, 259, 260, 261, 262, and 274 corresponding to subtilisin BPN'. Such positions are hereafter collectively referred to as the "clip site protection positions."

Preferably the positions are selected from 13, 14, 15, 16, 18, 19, 20, 21, 158, 159, 160, 161, 162, 163, 164, 165, 170, 186, 191, 192, 193, 194, 196, 259, 260, 261, and 262 corresponding to subtilisin BPN'. More preferably, the positions are selected from 14, 15, 16, 18, 19, 20, 21, 158, 159, 160, 161, 162, 163, 164, 165, 170, 186, 191, 192, 193, 194, 196, 259, 260, 261, and 262 corresponding to subtilisin BPN'. Still more preferably, the positions are selected from 18, 19, 20, 21, 158, 159, 160, 161, 162, 163, 164, 165, 170, 186, 191, 192, 193, 194, 196, 259, 260, 261, and 262 corresponding to subtilisin BPN'. Even more preferably, the positions are selected from 158, 159, 160, 161, 162, 163, 164, 165, 170, 186, 191, 192, 193, 194, 196, 259, 260, 261, and 262 corresponding to subtilisin BPN'. Within this group, the positions are more preferably selected from 158, 159, 160, 161, 162, 163, 164, 165, 170, 191, 192, 193, 194, 261, and 262 corresponding to subtilisin BPN'. More preferably, the positions are selected from 158, 159, 160, 161, 162, 163, 164, 192, 193, 194, 261, and 262 corresponding to subtilisin BPN'. Most preferably, the positions are selected from 160, 161, 162, 163, and 261 corresponding to subtilisin BPN'.

In a preferred embodiment of the present invention, the protease moiety comprises a modified sequence of a parent amino acid sequence. The parent amino acid sequence may be any of the above proteases described above, with the same preferred limitations as described above. In this embodiment, the parent amino acid sequence is substituted at one or more of the parent amino acid residues with a substituting amino acid to produce a protease moiety suitable for attachment with one or more of the present addition moieties. In accordance with the present invention, the substitution should be made at one or more positions at one or more of the clip site protection positions. The clip site protection positions, and preferred limitations thereof, are described above.

In order to best achieve selective attachment at one or more of the clip site protection positions of one or more addition moieties to the protease moiety, the substitution should be with a substituting amino acid which does not occur in (is unique to) the parent amino acid sequence. In this respect, any substituting amino acid which is unique to the parent amino acid sequence may be utilized. For example, because a cysteine residue does not occur in the wild-type amino acid sequence for subtilisin BPN', a substitution of subtilisin BPN' with one or more cysteine residues at one or more of the clip site protection positions is suitable for the present invention. Wherein a cysteine residue occurs at a position other than a clip site protection position of the parent amino acid sequence, it is preferable to substitute another amino acid residue for in each of those positions to enable selective coupling with one or more addition moieties at a clip site protection position. Cysteine is the most preferred substituting amino acid for substitution at one or more of the clip site protection positions.

Other preferred substituting amino acids include lysine. Wherein the substituting amino acid is lysine, it is preferred to mutate lysine residues which occur at positions other than a clip site protection position of the parent amino acid sequence to another amino acid residue such that functionalization of one or more of the lysine residues at a clip site protection position is selective. For example, a lysine residue occurs at position 170 of subtilisin BPN' which is a clip site protection position as defined herein. Site-selective mutation of all other lysine residues occurring in the subtilisin BPN' sequence may be performed followed by selective functionalization of the lysine residue at position 170 with an addition moiety. Alternatively, amino acid residues at any of the clip site protection positions may be mutated to lysine (for example) followed by selective functionalization at those positions by an addition moiety.

Addition Moieties

The protease conjugates of the present invention comprise one or more addition moieties wherein each of the addition moieties is covalently attached to one of the amino acid residues at a clip site protection position as described herein. The addition moiety may be any chemical structure. Preferably, the addition moiety sterically hinders the clip site protection position to which it is attached, or any other clip site protection position as defined herein. Non-limiting examples of addition moieties include organic molecules including, but not limited to, molecules having a molecular weight of less than about 1600, preferably less than about 800, more preferably less than about 400, and most preferably less than about 300; polypeptides; and polymers. As used herein, the term "polypeptide" means a molecule comprising two or more amino acid residues. As used herein, the term "polymer" means any molecule which comprises two or more identical (preferably five or more identical) monomer units.

Preferably, the addition moiety has the structure:

wherein X is selected from nil and a linking moiety; $R_1$ is selected from the group consisting of nil, a first polypeptide, and a first polymer; and $R_2$ is selected from the group consisting of nil, a second polypeptide, and a second polymer, wherein at least one of X, $R_1$, and $R_2$ is not nil.

Preferably, the protease conjugate comprises from 1 to about 15, more preferably from about 2 to about 10, and most preferably from about 1 to about 5 addition moieties.

Wherein $R_1$ and $R_2$ are each, independently, polypeptide moieties or polymer moieties, $R_1$ and $R_2$ may be identical or different. Preferably, wherein $R_1$ is a polypeptide moiety, $R_2$ is selected from nil and a polypeptide moiety, and is most preferably nil. Most preferably, wherein $R_1$ is a polypeptide moiety, $R_2$ is selected from nil and an identical polypeptide moiety, and is most preferably nil. Preferably, wherein $R_1$ is a polymer moiety, $R_2$ is selected from nil and a polymer moiety. Most preferably, wherein $R_1$ is a polymer moiety, $R_2$ is selected from nil and an identical polymer moiety. Wherein at least one of $R_1$ and $R_2$ are respectively, the first polymer and the second polymer, then X is preferably not nil.

Polypeptide Moieties

The polypeptide moieties described herein include those comprising two or more amino acid residues. Preferred polypeptide moieties are selected from proteins, including enzymes. Preferred enzymes include proteases, cellulases, lipases, amylases, peroxidases, microperoxidases, hemicellulases, xylanases, phospholipases, esterases, cutinases, pectinases, keratinases, reductases (including, for example, NADH reductase), oxidases, phenoloxidases, lipoxygenases, ligninases, pullulanases, tannases, pentosanases, malanases, b-glucanases, arabinosidases, hyaluronidase, chondroitinase, laccases, transferases, isomerases (including, for example, glucose isomerase and xylose isomerase), lyases, ligases, synthetases, and fruit-based enzymes (including, for example, papain). More preferred enzymes for use as polypeptide moieties include proteases, cellulases, amylases, lipases, and fruit-based enzymes, with proteases being even more preferred.

Examples of lipases for use as a polypeptide moiety include those derived from the following microorganisms: Humicola, Pseudonomas, Fusarium, Mucor, Chromobacterium, Aspergillus, Candida, Geotricum, Penicillium, Rhizopus, and Bacillus.

Examples of commercial lipases include Lipolase®, Lipolase Ultra®, Lipozyme®, Palatase®, Novozym435®, and Lecitase® (all of which are commercially available from Novo Nordisk, Copenhagen, Denmark), Lumafast® (commercially available from Genencor, Int., Rochester, N.Y.), and Lipomax® (Genencor, Int.).

Examples of proteases for use as the polypeptide moiety include serine proteases, chymotrypsin, and elastase-type enzymes. The most preferred proteases for use as a polypeptide moiety include serine proteases, as were defined herein above in the discussion of "protease moieties".

Most preferably, wherein the polypeptide moiety is a serine protease, the polypeptide moiety carries, independently, the definition of a protease moiety as described herein above. Preferably, as described above, the polypeptide moiety has a modified amino acid sequence of a parent amino acid sequence wherein the modification is in one or more of the clip site protection positions as described herein above (which parent amino acid sequence may be referred to as a "second" parent amino acid sequence). In this instance, one of the linking moiety (wherein the linking moiety is not nil) or the protease moiety (wherein the linking moiety is nil) is covalently attached to the polypeptide moiety through one of the substituting amino acids present in one of the clip site protection positions of the polypeptide moiety. Wherein the polypeptide moiety is a serine protease, the same preferred, more preferred, and most preferred groupings of clip site protection positions apply as are described herein above for protease moieties and their corresponding parent amino acid sequences.

Most preferably, wherein the polypeptide moiety is a serine protease, the polypeptide moiety and the protease moiety are equivalent moieties. In this instance, the polypeptide moiety and the protease moiety are most preferably attached through a disulfide bridge, wherein X is nil, and most preferably, $R_2$ is nil.

Polymer Moieties

The addition moieties herein may comprise a polymer moiety. As used herein, the term polymer moiety means any molecule which comprises two or more identical (preferably five or more identical) monomer units. Examples of suitable polymer moieties include polyalkylene oxides, polyalcohols, polyvinyl alcohols, polycarboxylates, polyvinylpyrrolidones, celluloses, dextrans, starches, glycogen, agaroses, guar gum, pullulan, inulin, xanthan gum, carrageenan, pectin, alginic acid hydrosylates, and hydrosylates of chitosan. Preferred polyalkylene oxides include polyethylene glycols, methoxypolyethylene glycols, and polypropylene glycols. Preferred dextrans include carboxymethyldextrans. Preferred celluloses include methylcellulose, carboxymethylcellulose, ethylcellulose, hydroxyethyl cellulose, carboxyethyl cellulose, and hydroxypropylcellulose. Preferred starches include hydroxyethyl starches and hydroxypropyl starches. The more preferred polymers are polyalkylene oxides. The most preferred polymer moiety is polyethylene glycol.

Wherein $R_1$ and $R_2$ are each, independently, polymer moieties, $R_1$ and $R_2$ preferably has a collective molecular weight (i.e., molecular weight of $R_1$ plus molecular weight of $R_2$) of from about 0.2 kD (kilodaltons) to about 40 kD, more preferably from about 0.5 kD to about 40 kD, even more preferably from about 0.5 kD to about 20 kD, and most preferably from about 1 kD to about 10 kD.

Wherein $R_1$ and $R_2$ are each polymer moieties, $R_1$ and $R_2$ each, independently, preferably have a molecular weight of about 0.1 kD to about 20 kD, more preferably from about 0.25 kD to about 20 kD, even more preferably from about 0.5 kD to about 10 kD, and most preferably from about 0.5 kD to about 5 kD.

Wherein $R_1$ and $R_2$ are each polymer moieties, the ratio of the molecular weights of $R_1$ to $R_2$ preferably ranges from about 1:10 to about 10:1, more preferably from about 1:5 to about 5:1, and most preferably from about 1:3 to about 3:1.

Wherein $R_1$ is a polymer moiety and $R_2$ is nil, $R_1$ preferably has a molecular weight of from about 0.1 kD to about 40 kD, more preferably about 0.5 kD to about 40 kD, even more preferably from about 0.5 kD to about 20 kD, and most preferably from about 1 kD to about 10 kD.

Linking Moieties

As used herein, X may be nil or a linking moiety which is optionally covalently attached to one or more polypeptide moieties or one or more polymer moieties, or both, and is also covalently attached to an amino acid residue at one of the clip site protection positions of the protease moiety. The linking moiety may be, generally, any small molecule, i.e., a molecule having a molecular weight of less than about 1600, preferably less than about 800, more preferably less than about 400, and most preferably less than about 300. The most preferred linking moieties include those capable of being covalently bound to a cysteine residue or a lysine residue, most preferably a cysteine residue.

Examples of linking moieties and related chemistry are disclosed in U.S. Pat. No. 5,446,090, Harris, issued Aug. 29, 1995; U.S. Pat. No. 5,171,264, Merrill, issued Dec. 15, 1992; U.S. Pat. No. 5,162,430, Rhee et al., issued Nov. 10, 1992; U.S. Pat. No. 5,153,265, Shadle et al., issued Oct. 6, 1992; U.S. Pat. No. 5,122,614, Zalipsky, issued Jun. 16, 1992; Goodson et al., "Site-Directed Pegylation of Recombinant Interleukin-2 at its Glycosylation Site", *Biotechnology*, Vol. 8, No. 4, pp. 343–346 (1990); Kogan, "The Synthesis of Substituted Methoxy-Poly(ethylene glycol) Derivatives Suitable for Selective Protein Modification", *Synthetic Communications*, Vol. 22, pp. 2417–2424 (1992); and Ishii et al., "Effects of the State of the Succinimido-Ring on the Fluorescence and Structural Properties of Pyrene Maleimide-Labeled aa-Tropomyosin", *Biophysical Journal*, Vol. 50, pp. 75–80 (1986). The most preferred linking moiety is substituted (for example, alkyl) or unsubstituted succinimide.

As further examples, the following non-limiting reagents may be utilized to form the linking moiety: N-[alpha-maleimidoacetoxy]succinimide ester; N-5-azido-2-nitrobenzoyloxysuccinimide; bismaleimidohexane; N-[beta-maleimidopropyloxy]succinimide ester; bis[2-(succinimidyloxycarbonyloxy)-ethyl]sulfone; bis[sulfosuccinimidyl]suberate; 1,5-difluoro-2,4-dintrobenzene; dimethlyadipimate.2HCl; dimethylpimelimidate.2HCl; dimethylsuberimidate.2HCl; disuccinimidyl glutarate; disuccinimidyl suberate; m-maleimidobenzoyl-N-hydroxysuccinimide ester; N-hydroxysuccinimidyl-4-azidosalicylic acid; N-succinimidyl-6-[4'-azido-2'-nitrophenylamino]hexanoate; N-hydroxysuccinimidyl 2,3-dibromopropionate; succinimidyl 4-[N-maleimidomethyl]cyclohexane-1-carboxylate; succinimidyl 4-(p-maleimidophenyl)-butyrate; succinimidyl-6-[(beta-maleimidopropionamido)hexanoate]; bis[2-(sulfosuccinimidyloxycarbonyloxy)-ethyl]sulfone; N-[gamma-maleimidobutyryloxy]sulfosuccinimide ester; N-hydroxysulfosuccinimidyl-4-azidobenzoate; N-[kappa-maleimidoundecanoyloxy]sulfosuccinimide ester; m-maleimidobenzoyl-N-hydroxysulfosuccinimide ester; sulfosuccinimidyl[4-azidosalicylamido]hexanoate; sulfosuccinimidyl 7-azido-4-methylcoumarin-3-acetate; sulfosuccinimidyl 6-[4'-azido-2'-nitrophenylamino]hexanoate; sulfosuccinimidyl 4-[p-azidophenyl]butyrate; sulfosuccinimidyl[4-iodoacetyl]aminobenzoate; sulfosuccinimidyl 4-[N-maleimidomethyl]cyclohexane-1-carboxylate; and sulfosuccinimidyl 4-(p-maleimidophenyl)-butyrate. Each of these reagents is commercially available from Pierce Chemical Co., Rockford, Ill.

Optional Moieties

The protease conjugate may additionally comprise one or more other chemical structures, including (for example) one or more small molecules, polypeptides, and/or polymers attached to other residues of the protease not herein exemplified or even at a clip site protection position not bearing an addition moiety (herein referred to as "supplementary moieties"). Supplementary moieties may include polypeptide moieties, polymer moieties, and linking moieties as described herein above. Additionally, for example, one or more polymers (most preferably polyethylene glycol) having a molecular weight of from about 100 Da to about 5000 Da, preferably from about 100 Da to about 2000 Da, more preferably from about 100 Da to about 1000 Da, still more preferably from about 100 Da to about 750 Da, and most preferably about 300 Da may be covalently attached to the protease moiety herein at residues other than those exemplified herein. Such polymer moieties may be attached directly to the protease moiety herein, at any location of the protease moiety, using techniques as described herein and as well-known in the art (including through a linking moiety as described herein). Non-limiting examples of polymer conjugation of this optional type is set forth in WO 99/00849, Olsen et al., Novo Nordisk A/S, published Jan. 7, 1999.

Method of Making

The protease moieties having a substitution in one or more of the clip site protection positions (or any other location of the moiety) are prepared by mutating the nucleotide sequences that code for a parent amino acid sequence. Such methods are well-known in the art; a non-limiting example of one such method is set forth below:

A phagemid (pSS-5) containing the wild-type subtilisin BPN' gene (Mitchison, C. and J. A. Wells, "Protein Engineering of Disulfide Bonds in Subtilisin BPN'", *Biochemistry*, Vol. 28, pp. 480–4815 (1989) is transformed into *Escherichia coli dut-ung*-strain CJ236 and a single stranded uracil-containing DNA template is produced using the VCSM13 helper phage (Kunkel et al., "Rapid and Efficient Site-Specific Mutagenesis Without Phenotypic Selection", *Methods in Enzymology*, Vol 154, pp. 367–382 (1987), as modified by Yuckenberg et al., "Site-Directed in vitro Mutagenesis Using Uracil-Containing DNA and Phagemid Vectors", *Directed Mutagenesis— A Practical Approach*, McPherson, M. J. ed., pp. 27–48 (1991). Primer site-directed mutagenesis modified from the method disclosed in Zoller, M. J., and M. Smith, "Oligonucleotide—Directed Mutagenesis Using M13—Derived Vectors: An Efficient and General Procedure for the Production of Point Mutations in any Fragment of DNA", *Nucleic Acids Research*, Vol. 10, pp. 6487–6500 (1982) is used to produce all mutants (essentially as presented by Yuckenberg et al., supra).

Oligonucleotides are made using a 380B DNA synthesizer (Applied Biosystems Inc.). Mutagenesis reaction products are transformed into *Escherichia coli* strain MM294 (American Type Culture Collection *E. coli* 33625). All mutations are confirmed by DNA sequencing and the isolated DNA is transformed into the *Bacillus subtilis* expression strain PG632 (Saunders et al., "Optimization of the Signal-Sequence Cleavage Site for Secretion from *Bacillus subtilis* of a 34-Amino Acid Fragment of Human Parathyroid Hormone", *Gene*, Vol. 102, pp. 277–282 (1991) and Yang et al., "Cloning of the Neutral Protease Gene of *Bacillus subtilis* and the Use of the Cloned Gene to Create an in vitro—Derived Deletion Mutation", *Journal of Bacteriology*, Vol. 160, pp. 15–21 (1984).

Fermentation is as follows. *Bacillus subtilis* cells (PG632) containing the protease of interest are grown to mid-log phase in one liter of LB broth containing 10 g/L glucose, and inoculated into a Biostat C fermentor (Braun Biotech, Inc., Allentown, Pa.) in a total volume of 9 liters. The fermentation medium contains yeast extract, casein hydrosylate, soluble—partially hydrolyzed starch (Maltrin M-250), antifoam, buffers, and trace minerals (see "Biology of Bacilli: Applications to Industry", Doi, R. H. and M. McGloughlin, eds. (1992)). The broth is kept at a constant pH of 7.5 during the fermentation run. Kanamycin (50 μg/mL) is added for antibiotic selection of the mutagenized plasmid. The cells are grown for 18 hours at 37° C. to an $A_{600}$ of about 60 and the product harvested.

The fermentation broth is taken through the following steps to obtain pure protease. The broth is cleared of *Bacillus subtilis* cells by tangential flow against a 0.16 μm membrane. The cell-free broth is then concentrated by ultrafiltration with a 8,000 molecular weight cut-off membrane. The pH is adjusted to 5.5 with concentrated MES buffer (2-(N-morpholino)ethanesulfonic acid). The protease is further purified by cation exchange chromatography with S-sepharose and elution with NaCl gradients. See Scopes, R. K., "Protein Purification Principles and Practice", Springer-Verlag, New York (1984)

ApNA assay (DelMar et al., *Analytical Biochemistry*, Vol. 99, pp. 316–320 (1979)) is used to determine the active protease concentration for fractions collected during gradient elution. This assay measures the rate at which p-nitroaniline is released as the protease hydrolyzes the soluble synthetic substrate, succinyl-alanine-alanine-proline-phenylalanine-p-nitroaniline (sAAPF-pNA). The rate of production of yellow color from the hydrolysis reaction is measured at 410 nm on a spectrophotometer and is proportional to the active protease moiety concentration. In addition, absorbance measurements at 280 nm are used to determine the total protein concentration. The active protease/total-protein ratio gives the protease purity, and is used to identify fractions to be pooled for the stock solution.

To avoid autolysis of the protease during storage, an equal weight of propylene glycol is added to the pooled fractions obtained from the chromatography column. Upon completion of the purification procedure the purity of the stock protease solution is checked with SDS-PAGE (sodium dodecyl sulfate polyacrylamide gel electrophoresis) and the absolute enzyme concentration is determined via an active site titration method using trypsin inhibitor type II-T: turkey egg white (Sigma Chemical Company, St. Louis, Mo.).

In preparation for use, the protease stock solution is eluted through a Sephadex-G25 (Pharmacia, Piscataway, N.J.) size exclusion column to remove the propylene glycol and exchange the buffer. The MES buffer in the enzyme stock solution is exchanged for 0.01 M $KH_2PO_4$ solution, pH 5.5.

With the protease prepared it may be utilized for functionalization with one or more addition moieties to produce the protease conjugate. The precursor to the addition moiety (the precursor to the addition moiety reacts with the precursor to the protease moiety to form the protease conjugate which is comprised of the addition moiety and the protease moiety) is preferably activated to enhance reactivity with the precursor to the protease moiety. Such activation is well-known in the art. Non-limiting examples of methods of protease conjugate preparation are provided below.

EXAMPLE 1

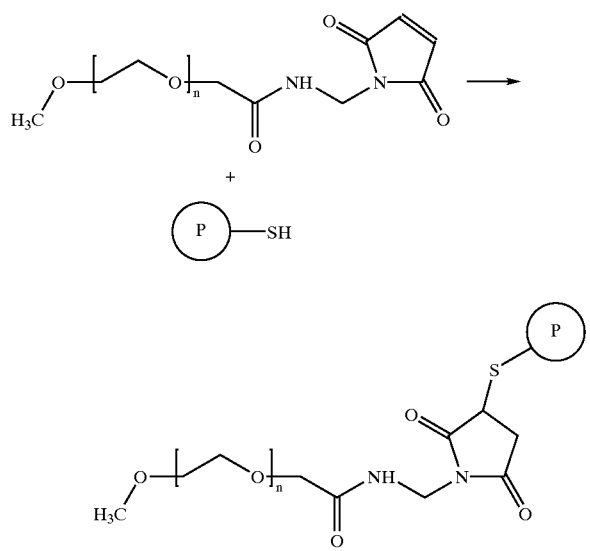

A protease comprising a cysteine residue at one of the clip site protection positions is coupled with a polymer moiety according to the above scheme using the following method (wherein "P" represents the protease moiety minus the thiol group resulting from the cysteine substitution and n is the number of repeating monomer units of the polyethylene glycol (for example, n=77).

A variant of subtilisin BPN' with a substitution of leucine for tyrosine at position 217 and a substitution of cysteine for serine at position 161 is prepared. A concentration of approximately 2 mg/mL in phosphate buffer (pH 5.5) of the variant is achieved. The pH is then raised to 7.5 with dilute sodium hydroxide. The variant is mixed with the monomethyl polyethylene glycol maleimide at a 25:1 activated polymer to variant excess. After one hour of mixing at ambient temperature, the pH of the mixture is adjusted to 5.5 with dilute phosphoric acid and filtered through a molecular weight cut-off ultrafilter to remove excess polymer. The concentrate contains the purified protease conjugate.

EXAMPLE 2

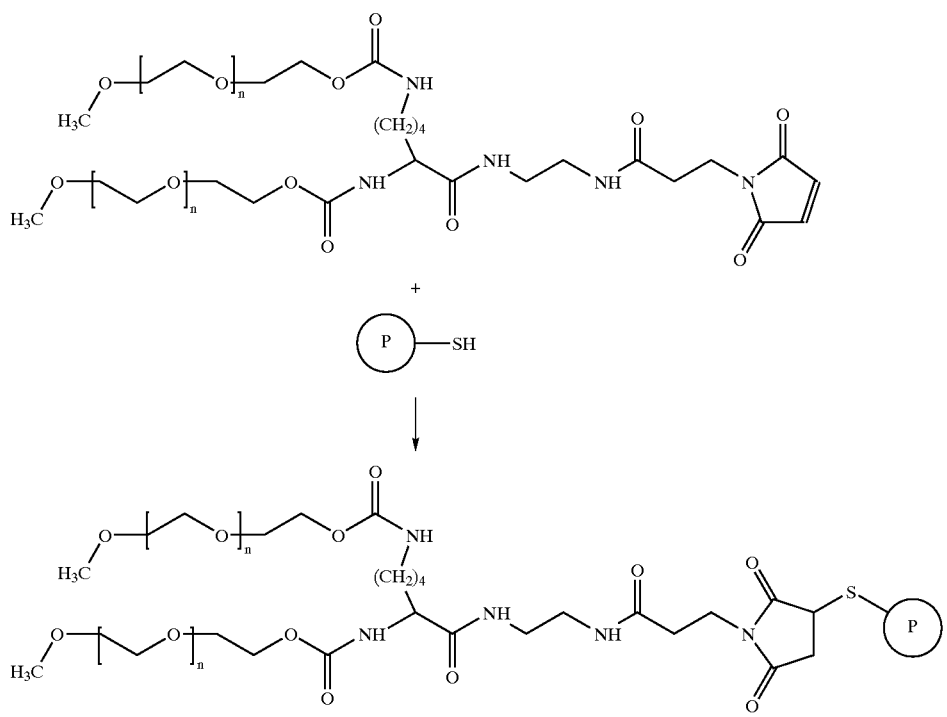

A protease moiety comprising a cysteine residue at one of the clip site protection positions is coupled with a polymer moiety according to the above scheme using the following method (wherein "P" represents the protease moiety minus the thiol group resulting from the cysteine substitution and n is the number of repeating monomer units of each polyethylene glycol (e.g., n=77)).

A variant of subtilisin BPN' with a substitution of leucine for tyrosine at position 217 and a substitution of cysteine for phenylalanine at position 261 is prepared. A concentration of approximately 2 mg/mL in phosphate buffer (pH 5.5) of the variant is achieved. The pH is then raised to 7.5 with dilute sodium hydroxide. The variant is mixed with the dimethyl polyethylene glycol maleimide at a 25:1 activated polymer to variant excess. After one hour of mixing at ambient temperature, the pH of the mixture is adjusted to 5.5 with dilute phosphoric acid and filtered through a molecular weight cut-off ultrafilter to remove excess polymer. The concentrate contains the purified protease conjugate.

EXAMPLE 3

Succinimide-protected polymer is coupled selectively to lysine in one or more of the clip site protection positions (wherein "MPEG" and "PEGM" are equivalent and represent monomethyl polyethylene glycols and wherein "P" represents the protease moiety minus the lysine amine group shown):

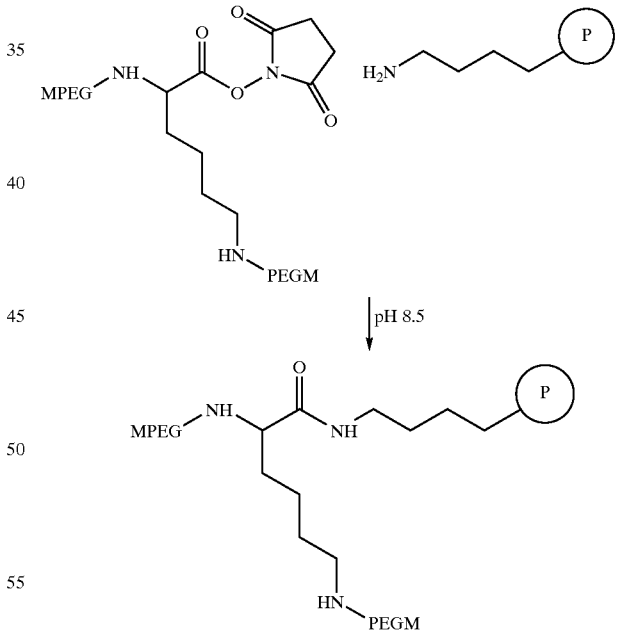

EXAMPLE 4

Carbodiimide-protected polymer is coupled selectively to lysine in one or more of the clip site protection positions (wherein "MPEG" and "PEGM" are equivalent and represent monomethyl polyethylene glycols, "P" represents the protease moiety minus the lysine amine group shown, and X and X' are side chains comprising the carbodiimide moiety, for example, alkyls):

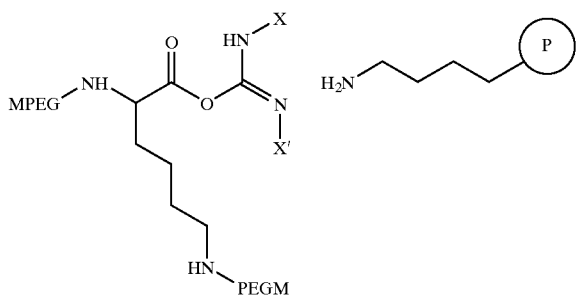

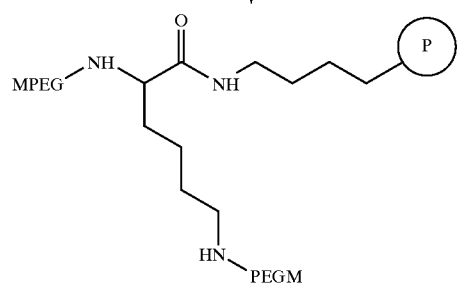

EXAMPLE 5

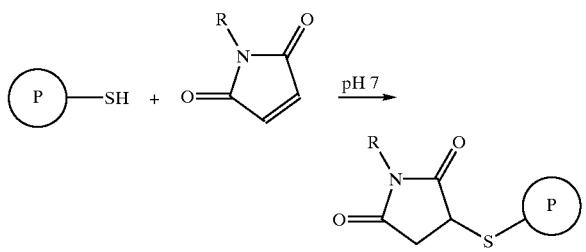

A protease moiety comprising a cysteine residue in one of the clip site protection positions is coupled with an alkyl maleimide using the following method (wherein "P" represents the protease moiety minus the thiol group resulting from the cysteine substitution and "R" is an alkyl-group). In this example, $R_1$ and $R_2$ are each nil and the linking moiety is derived from the alkyl maleimide.

A variant of subtilisin BPN' with a substitution of leucine for tyrosine at position 217 and a substitution of cysteine for serine at position 163 is prepared. A 20 mL solution of the variant is prepared at a concentration of approximately 1 mg/mL in 0.01 M $KH_2PO_4$ buffer (pH 7). To this solution, an 1.5 equivalents of alkyl maleimide (for example, methyl maleimide) is added to the solution. The solution is gently mixed at ambient temperature for approximately one hour. The resulting protease conjugate is obtained from the solution by standard methods.

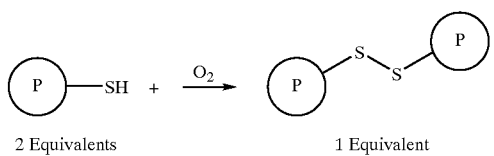

2 Equivalents    1 Equivalent

A protease moiety comprising a cysteine residue at one of the clip site protection positions forms a dimer using the following method (wherein "P" represents the protease moiety minus the thiol group resulting from the cysteine substitution). In this example, the protease moiety and the polypeptide moiety are equivalent (and X is nil).

A variant of subtilisin BPN' with a substitution of leucine for tyrosine at position 217 and a substitution of cysteine for serine at position 163 is prepared. A 20 mL solution of the variant is prepared at a concentration of approximately 1 mg/mL in 0.01 M $KH_2PO_4$ buffer (pH 8.6). Oxygen is gently bubbled through the solution at ambient temperature for approximately one hour to form the desired protease conjugate dimer. The resulting protease conjugate is obtained from the solution by standard methods.

Analytical Methods

The present protease conjugates may be tested for enzymatic activity and immunogenic response using the following methods, both of which are known to one skilled in the art. Other methods well-known in the art may alternatively be used.

Protease Conjugate Activity

The protease activity of a protease conjugate of the present invention may be assayed by methods which are well-known in the art. Two such methods are set forth herein below:

Skin Flake Activity Method

Using Scotch®#3750G tape, human skin flakes are stripped from the legs of a subject repeatedly until the tape is substantially opaque with flakes. The tape is then cut into 1 inch by 1 inch squares and set aside. In a 10 mm by 35 mm petri dish, 2 mL of 0.75 mg/mL of a control enzyme (for example, subtilisin BPN') or the protease conjugate to be tested is added in 0.01 M $KH_2PO_4$ pH 5.5 buffer. To this solution 1 mL of 2.5% sodium laurate pH 8.6 solution is added. The solution is gently mixed on a platform shaker. The previously prepared tape square is soaked in the solution (flake side up) for ten minutes continuing gentle mixing. The tape square is then rinsed gently in tap water for fifteen seconds. Stevenel Blue Stain (3 mL, commercially available from Sigma Chemical Co., St. Louis, Mo.) is pipetted into a clean petri dish. The rinsed tape square is placed into the stain for three minutes (flake side up) with gentle mixing. The tape square is removed from the stain and rinsed consecutively in two beakers of 300 mL distilled water, for fifteen seconds per rinse. The tape square is allowed to air-dry. The color intensity between the tape square obtained from the control enzyme and the tape square obtained from the protease conjugate is compared visually or by using a chromameter. Relative to the control enzyme tape square, a protease conjugate tape square showing less color intensity is indicative of a protease conjugate having higher activity.

Dyed Collagen Activity Method

Combine 50 mL of 0.1 M tris buffer (tris-hydroxymethyl-aminomethane) containing 0.01 M $CaCl_2$ to give pH 8.6, and 0.5 g azocoll (azo dye impregnated collagen, commercially available from Sigma Chemical Co., St. Louis, Mo.). Incubate this mixture at 25° C. while gently mixing with a platform shaker. Filter 2 mL of the mixture through a 0.2 micron syringe filter and read absorbance of the mixture at 520 nm to zero a spectrophotometer. Add 1 ppm of a control enzyme (for example, subtilisin BPN') or the protease conjugate to be tested to the remaining 48 mL of tris/azocoll mixture. Filter 2 mL of the control/protease conjugate containing solution through a 0.2 micron syringe filter every two minutes for a total of ten minutes. For each filtered sample, read the absorbance immediately at 520 nm. Plot the results against time. The slopes of the control and the test conjugate are indicative of relative activities of the samples. A higher slope is indicative of a higher activity. The test protease conjugate activity (slope) may be expressed as a percent of the control activity (slope).

Mouse Intranasal Test for Immunogenicity

The immunogenic potential of the protease conjugates of the present invention may be determined using a methods known in the art or by the Mouse Intranasal Test for Immunogenicity presented herein below. This test is similar to the assays described in Robinson et al., "Specific Antibody Responses to Subtilisin Carlsberg (Alcalase) in Mice: Development of an Intranasal Exposure Model", *Fundamental and Applied Toxicology*, Vol. 34, pp. 15–24 (1996) and Robinson et al., "Use of the Mouse Intranasal Test (MINT) to Determine the Allergenic Potency of Detergent Enzymes: Comparison to the Guinea Pig Intratracheal (GPIT) Test", *Toxicological Science*, Vol. 43, pp. 39–46 (1998), both of which assays may be utilized in place of the test set forth herein below.

Female BDF1 mice (Charles River Laboratories, Portage, Mich.) weighing from about 18 to about 20 grams are utilized in the test. The mice are quarantined one week prior to dosing. The mice are housed in cages with wood chip bedding in rooms controlled for humidity (30–70%), temperature (67–77° F.) and 12 hour light and dark cycles. The mice are fed Purina® mouse chow (Purina Mills, Richmond, Ind.) and water ad libitum.

The potential antigen to be tested (either subtilisin BPN' as positive control or a protease conjugate of the present invention) is dosed to a group of five mice. Prior to dosing, each mouse is anesthetized by an intraperitoneal (i.p.) injection of a mixture of Ketaset (88.8 mg/kg) and Rompun (6.67 mg/kg). The anesthetized animal is held in the palm of the hand, back down, and dosed intranasally with 5 mL protease in buffer solution (0.01 M $KH_2PO_4$, pH 5.5). While each group receives the same dosage, various dosages may be tested. Dosing solutions are gently placed on the outside of each nostril and inhaled by the mouse. Dosing is repeated on days 3, 10, 17, and 24.

Serum samples are collected on day 29. Enzyme-specific IgG1 antibody in mouse serum is measured by an antigen capture ELISA method. Immunogenicities of the protease conjugate may be compared against those of subtilisin BPN' using standard $ED_{50}$ values.

Compositions of the Present Invention

The protease conjugates herein can be used in any application in which is suitable for the respective parent protease. One such example includes cleaning compositions. Because of the desirable reduced immunogenicity properties of the present protease conjugates, the protease conjugates may further be used in applications which have historically minimally benefited from the use of proteases. Examples of such applications include those in which the protease conjugate necessarily comes in close contact with mammalian skin (especially human skin), such as with the use of personal care compositions.

Cleaning Compositions

The protease conjugates may be utilized in cleaning compositions including, but not limited to, laundry compositions, hard surface cleansing compositions, light duty cleaning compositions including dish cleansing compositions, and automatic dishwasher detergent compositions.

The cleaning compositions herein comprise an effective amount of one or more protease conjugates of the present invention and a cleaning composition carrier.

As used herein, "effective amount of protease conjugate", or the like, refers to the quantity of protease conjugate necessary to achieve the proteolytic activity necessary in the specific cleaning composition. Such effective amounts are readily ascertained by one of ordinary skill in the art and is based on many factors, such as the particular protease conjugate used, the cleaning application, the specific composition of the cleaning composition, and whether a liquid or dry (e.g., granular, bar) composition is required, and the like. Preferably, the cleaning compositions comprise from about 0.0001% to about 10%, more preferably from about 0.001% to about 1%, and most preferably from about 0.01% to about 0.1% of one or more protease conjugates of the present invention. Several examples of various cleaning compositions wherein the protease conjugates may be employed are discussed in further detail below.

In addition to the present protease conjugates, the present cleaning compositions further comprise a cleaning composition carrier comprising one or more cleaning composition materials compatible with the protease conjugate. The term "cleaning composition material", as used herein, means any material selected for the particular type of cleaning composition desired and the form of the product (e.g., liquid, granule, bar, spray, stick, paste, gel), which materials are also compatible with the protease conjugate used in the composition. The specific selection of cleaning composition materials is readily made by considering the surface material to be cleaned, the desired form of the composition for the cleaning condition during use (e.g., through the wash detergent use). The term "compatible", as used herein, means the cleaning composition materials do not reduce the proteolytic activity of the protease conjugate to such an extent that the protease is not effective as desired during normal use situations. Specific cleaning composition materials are exemplified in detail hereinafter.

The protease conjugates of the present invention may be used in a variety of detergent compositions wherein high sudsing and good cleansing is desired. Thus the protease conjugates can be used with various conventional ingredients to provide fully-formulated hard-surface cleaners, dishwashing compositions, fabric laundering compositions, and the like. Such compositions can be in the form of liquids, granules, bars, and the like. Such compositions can be formulated as "concentrated" detergents which contain as much as from about 30% to about 60% by weight of surfactants.

The cleaning compositions herein may optionally, and preferably, contain various surfactants (e.g., anionic, nonionic, or zwitterionic surfactants). Such surfactants are typically present at levels of from about 5% to about 35% of the compositions.

Nonlimiting examples of surfactants useful herein include the conventional $C_{11}$–$C_{18}$ alkyl benzene sulfonates and primary and random alkyl sulfates, the $C_{10}$–$C_{18}$ secondary (2,3) alkyl sulfates of the formulas $CH_3(CH_2)_x(CHOSO_3)^-M^+)CH_3$ and $CH_3(CH_2)_y(CHOSO_3^-M^+)CH_2CH_3$ wherein x and (y+1) are integers of at least about 7, preferably at least about 9, and M is a water-solubilizing cation, especially sodium, the $C_{10}$–$C_{18}$ alkyl alkoxy sulfates (especially EO 1–5 ethoxy sulfates), $C_{10}$–$C_{18}$ alkyl alkoxy carboxylates (especially the EO 1–5 ethoxycarboxylates), the $C_{10}$–$C_{18}$ alkyl polyglycosides, and their corresponding sulfated polyglycosides, $C_{12}$–$C_{18}$ a-sulfonated fatty acid esters, $C_{12}$–$C_{18}$ alkyl and alkyl phenol alkoxylates (especially ethoxylates and mixed ethoxy/propoxy), $C_{12}$–$C_{18}$ betaines and sulfobetaines ("sultaines"), $C_{10}$–$C_{18}$ amine oxides, and the like. The alkyl alkoxy sulfates (AES) and alkyl alkoxy carboxylates (AEC) are preferred herein. The use of such surfactants in combination with the amine oxide and/or betaine or sultaine surfactants is also preferred, depending on the desires of the formulator. Other conventional useful surfactants are listed in standard texts. Particularly useful surfactants include the $C_{10}$–$C_{18}$ N-methyl glucamides disclosed in U.S. Pat. No. 5,194,639, Connor et al., issued Mar. 16, 1993.

A wide variety of other ingredients useful in detergent cleaning compositions can be included in the compositions herein including, for example, other active ingredients, carriers, hydrotropes, processing aids, dyes or pigments, and solvents for liquid formulations. If an additional increment of sudsing is desired, suds boosters such as the $C_{10}$–$C_{16}$ alkolamides can be incorporated into the compositions, typically at about 1% to about 10% levels. The $C_{10}$–$C_{14}$ monoethanol and diethanol amides illustrate a typical class of such suds boosters. Use of such suds boosters with high sudsing adjunct surfactants such as the amine oxides, betaines and sultaines noted above is also advantageous. If desired, soluble magnesium salts such as $MgCl_2$, $MgSO_4$, and the like, can be added at levels of, typically, from about 0.1% to about 2%, to provide additional sudsing.

The liquid detergent compositions herein may contain water and other solvents as carriers. Low molecular weight primary or secondary alcohols exemplified by methanol, ethanol, propanol, and iso-propanol are suitable. Monohydric alcohols are preferred for solubilizing surfactants, but polyols such as those containing from about 2 to about 6 carbon atoms and from about 2 to about 6 hydroxy groups (e.g., 1,3-propanediol, ethylene glycol, glycerine, and 1,2-propanediol) can also be used. The compositions may contain from about 5% to about 90%, typically from about 10% to about 50% of such carriers.

The detergent compositions herein will preferably be formulated such that during use in aqueous cleaning operations, the wash water will have a pH between about 6.8 and about 11. Finished products thus are typically formulated at this range. Techniques for controlling pH at recommended usage levels include the use of, for example, buffers, alkalis, and acids. Such techniques are well known to those skilled in the art.

When formulating the hard surface cleaning compositions and fabric cleaning compositions of the present invention, the formulator may wish to employ various builders at levels from about 5% to about 50% by weight. Typical builders include the 1–10 micron zeolites, polycarboxylates such as citrate and oxydisuccinates, layered silicates, phosphates, and the like. Other conventional builders are listed in standard formularies.

Likewise, the formulator may wish to employ various additional enzymes, such as cellulases, lipases, amylases, and proteases in such compositions, typically at levels of from about 0.001% to about 1% by weight. Various detersive and fabric care enzymes are well-known in the laundry detergent art.

Various bleaching compounds, such as the percarbonates, perborates and the like, can be used in such compositions, typically at levels from about 1% to about 15% by weight. If desired, such compositions can also contain bleach activators such as tetraacetyl ethylenediamine, nonanoyloxybenzene sulfonate, and the like, which are also known in the art. Usage levels typically range from about 1% to about 10% by weight.

Soil release agents, especially of the anionic oligoester type, chelating agents, especially the aminophosphonates and ethylenediaminedisuccinates, clay soil removal agents, especially ethoxylated tetraethylene pentamine, dispersing agents, especially polyacrylates and polyasparatates, brighteners, especially anionic brighteners, suds suppressors, especially silicones and secondary alcohols, fabric softeners, especially smectite clays, and the like can all be used in such compositions at levels ranging from about 1% to about 35% by weight. Standard formularies and published patents contain multiple, detailed descriptions of such conventional materials.

Enzyme stabilizers may also be used in the cleaning compositions. Such enzyme stabilizers include propylene glycol (preferably from about 1% to about 10%), sodium formate (preferably from about 0.1% to about 1%) and calcium formate (preferably from about 0.1% to about 1%).

The present variants are useful in hard surface cleaning compositions. As used herein "hard surface cleaning composition" refers to liquid and granular detergent compositions for cleaning hard surfaces such as floors, walls, bathroom tile, and the like. Hard surface cleaning compositions of the present invention comprise an effective amount of one or more protease conjugates of the present invention, preferably from about 0.001% to about 10%, more preferably from about 0.01% to about 5%, and more preferably still from about 0.05% to about 1% by weight of protease conjugate of the composition. In addition to comprising one or more of the protease conjugates, such hard surface cleaning compositions typically comprise a surfactant and a water-soluble sequestering builder. In certain specialized products such as spray window cleaners, however, the surfactants are sometimes not used since they may produce a filmy and or streaky residue on the glass surface.

The surfactant component, when present, may comprise as little as 0.1% of the compositions herein, but typically the compositions will contain from about 0.25% to about 10%, more preferably from about 1% to about 5% of surfactant.

Typically the compositions will contain from about 0.5% to about 50% of a detergency builder, preferably from about 1% to about 10%.

Preferably the pH should be in the range of about 7 to 12. Conventional pH adjustment agents such as sodium hydroxide, sodium carbonate, or hydrochloric acid can be used if adjustment is necessary.

Solvents may be included in the compositions. Useful solvents include, but are not limited to, glycol ethers such as diethyleneglycol monohexyl ether, diethyleneglycol monobutyl ether, ethyleneglycol monobutyl ether, ethyleneglycol monohexyl ether, propyleneglycol monobutyl ether, dipropyleneglycol monobutyl ether, and diols such as 2,2,4-trimethyl-1,3-pentanediol and 2-ethyl-1,3-hexanediol. When used, such solvents are typically present at levels of from about 0.5% to about 15%, more preferably from about 3% to about 11%.

Additionally, highly volatile solvents such as iso-propanol or ethanol can be used in the present compositions to facilitate faster evaporation of the composition from surfaces when the surface is not rinsed after "full strength" application of the composition to the surface. When used, volatile solvents are typically present at levels of from about 2% to about 12% in the compositions.

EXAMPLES 7–12

Liquid Hard Surface Cleaning Compositions

|  | Ex. 7 | Ex. 8 | Ex. 9 | Ex. 10 | Ex. 11 | Ex. 12 |
|---|---|---|---|---|---|---|
| Protease Conjugate of Example 3 | 0.05% | 0.50% | 0.02% | 0.03% | 0.30% | 0.05% |
| EDTA | — | — | 2.90% | 2.90% | — | — |
| Sodium Citrate | — | — | — | — | 2.90% | 2.90% |
| $NaC_{12}$ Alkyl-benzene sulfonate | 1.95% | — | 1.95% | — | 1.95% | — |
| $NaC_{12}$ Alkylsulfate | — | 2.20% | — | 2.20% | — | 2.20% |
| $NaC_{12}$ (ethoxy) sulfate | — | 2.20% | — | 2.20% | — | 2.20% |
| $C_{12}$ Dimethylamine oxide | — | 0.50% | — | 0.50% | — | 0.50% |
| Sodium cumene sulfonate | 1.30% | — | 1.30% | — | 1.30% | — |
| Hexyl Carbitol | 6.30% | 6.30% | 6.30% | 6.30% | 6.30% | 6.30% |
| Water | 90.4% | 88.3% | 87.53% | 85.87% | 87.25% | 85.85% |

All formulas are adjusted to pH 7.

In another embodiment of the present invention, dishwashing compositions comprise one or more variants of the present invention. As used herein, "dishwashing composition" refers to all forms of compositions for cleaning dishes including, but not limited to, granular and liquid forms.

EXAMPLES 13–16

Liquid Dish Detergent

|  | Ex. 13 | Ex. 14 | Ex. 15 | Ex. 16 |
|---|---|---|---|---|
| Protease Conjugate of Example 1 | 0.05% | 0.50% | 0.02% | 0.40% |
| $C_{12}$–$C_{14}$ N-methyl glucamide | 0.90% | 0.90% | 0.90% | 0.90% |
| $C_{12}$ ethoxy (1) sulfate | 12.0% | 12.0% | 12.0% | 12.0% |
| 2-Methyl undecanoic acid | 4.50% | 4.50% | 4.50% | 4.50% |
| $C_{12}$ ethoxy (2) carboxylate | 4.50% | 4.50% | 4.50% | 4.50% |
| $C_{12}$ alcohol ethoxylate (4) | 3.00% | 3.00% | 3.00% | 3.00% |
| $C_{12}$ amine oxide | 3.00% | 3.00% | 3.00% | 3.00% |
| Sodium cumene sulfonate | 2.00% | 2.00% | 2.00% | 2.00% |
| Ethanol | 4.00% | 4.00% | 4.00% | 4.00% |
| $Mg^{2+}$ (as $MgCl_2$) | 0.20% | 0.20% | 0.20% | 0.20% |
| $Ca^{2+}$ (as $CaCl_2$) | 0.40% | 0.40% | 0.40% | 0.40% |
| Water | 65.45% | 65% | 65.48% | 65.1% |

All formulas are adjusted to pH 7.

EXAMPLES 17–19

Liquid Fabric Cleaning Compositions

|  | Ex. 17 | Ex. 18 | Ex. 19 |
|---|---|---|---|
| Protease Conjugate of Example 4 | 0.05% | 0.03% | 0.30% |
| Sodiuam $C_{12}$–$C_{14}$ alkyl sulfate | 20.0% | 20.0% | 20.0% |
| 2-Butyl octanoic acid | 5.0% | 5.0% | 5.0% |
| Sodium citrate | 1.0% | 1.0% | 1.0% |
| $C_{10}$ Alcohol ethoxylate (3) | 13.0% | 13.0% | 13.0% |
| Monoethanolamine | 2.50% | 2.50% | 2.50% |
| Water/propylene glycol/ethanol (100:1:1) | 58.45% | 58.47% | 58.20% |

Personal Care Compositions

The present protease conjugates are particularly suited for use in personal care compositions such as, for example, leave-on and rinse-off hair conditioners, shampoos, leave-on and rinse-off acne compositions, facial milks and conditioners, shower gels, soaps, foaming and non-foaming facial cleansers, cosmetics, hand, facial, and body lotions, moisturizers, patches, and masks, leave-on facial moisturizers, cosmetic and cleansing wipes, oral care compositions, catamenials, and contact lens care compositions. The present personal care compositions comprise one or more protease conjugates of the present invention and a personal care carrier.

To illustrate, the present protease conjugates are suitable for inclusion in the compositions described in the following references: U.S. Pat. No. 5,641,479, Linares et al., issued Jun. 24, 1997 (skin cleansers); U.S. Pat. No. 5,599,549, Wivell et al., issued Feb. 4, 1997 (skin cleansers); U.S. Pat. No. 5,585,104, Ha et al., issued Dec. 17, 1996 (skin cleansers); U.S. Pat. No. 5,540,852, Kefauver et al., issued Jul. 30, 1996 (skin cleansers); U.S. Pat. No. 5,510,050, Dunbar et al., issued Apr. 23, 1996 (skin cleansers); U.S. Pat. No. 5,612,324, Guang Lin et al., issued Mar. 18, 1997 (anti-acne preparations); U.S. Pat. No. 5,587,176, Warren et al., issued Dec. 24, 1996 (anti-acne preparations); U.S. Pat. No. 5,549,888, Venkateswaran, issued Aug. 27, 1996 (anti-acne preparations); U.S. Pat. No. 5,470,884, Corless et al., issued Nov. 28, 1995 (anti-acne preparations); U.S. Pat. No. 5,650,384, Gordon et al., issued Jul. 22, 1997 (shower gels); U.S. Pat. No. 5,607,678, Moore et al., issued Mar. 4, 1997 (shower gels); U.S. Pat. No. 5,624,666, Coffindaffer et al., issued Apr. 29, 1997 (hair conditioners and/or shampoos); U.S. Pat. No. 5,618,524, Bolich et al., issued Apr. 8, 1997 (hair conditioners and/or shampoos); U.S. Pat. No. 5,612,301, Inman, issued Mar. 18, 1997 (hair conditioners and/or shampoos); U.S. Pat. No. 5,573,709, Wells, issued Nov. 12, 1996 (hair conditioners and/or shampoos); U.S. Pat. No. 5,482,703, Pings, issued Jan. 9, 1996 (hair conditioners and/or shampoos); U.S. Pat. No. Re. 34,584, Grote et al., Reissued Apr. 12, 1994 (hair conditioners and/or shampoos); U.S. Pat. No. 5,641,493, Date et al., issued Jun. 24, 1997 (cosmetics); U.S. Pat. No. 5,605,894, Blank et al., issued Feb. 25, 1997 (cosmetics); U.S. Pat. No. 5,585,090, Yoshioka et al., issued Dec. 17, 1996 (cosmetics); U.S. Pat. No. 4,939,179, Cheney et al., issued Jul. 3, 1990 (hand, face, and/or body lotions); U.S. Pat. No. 5,607,980, McAtee et al., issued Mar. 4, 1997 (hand, face, and/or body lotions); U.S. Pat. No. 4,045,364, Richter et al., issued Aug. 30, 1977 (cosmetic and cleansing wipes); European Patent Application, EP 0 619 074, Touchet et al., published Oct. 12, 1994 (cosmetic and cleansing wipes); U.S. Pat. No. 4,975,217, Brown-Skrobot et al., issued Dec. 4, 1990 (cosmetic and cleansing wipes); U.S. Pat. No. 5,096,700, Seibel, issued Mar. 17, 1992 (oral cleaning compositions); U.S. Pat. No. 5,028,414, Sampathkumar issued Jul. 2, 1991 (oral cleaning compositions); U.S. Pat. No. 5,028,415, Benedict et al., issued Jul. 2, 1991 (oral cleaning compositions); U.S. Pat. No. 5,028,415, Benedict et al., issued Jul. 2, 1991 (oral cleaning compositions); U.S. Pat. No. 4,863,627, Davies et al., Sep. 5, 1989 (contact lens cleaning solutions); U.S. Pat. No. Re. 32,672, Huth et al, reissued May 24, 1988 (contact lens cleaning solutions); and U.S. Pat. No. 4,609,493, Schafer, issued Sep. 2, 1986 (contact lens cleaning solutions).

To further illustrate oral cleaning compositions of the present invention, a pharmaceutically-acceptable amount of one or more protease conjugates of the present invention is included in compositions useful for removing proteinaceous stains from teeth or dentures. As used herein, "oral cleaning compositions" refers to dentifrices, toothpastes, toothgels, toothpowders, mouthwashes, mouth sprays, mouth gels, chewing gums, lozenges, sachets, tablets, biogels, prophylaxis pastes, dental treatment solutions, and the like. Preferably, the oral cleaning compositions comprise from about 0.0001% to about 20% of one or more protease conjugates of the present invention, more preferably from about 0.001% to about 10%, more preferably still from about 0.01% to about 5%, by weight of the composition, and a pharmaceutically-acceptable carrier. As used herein, "pharmaceutically-acceptable" means that drugs, medicaments, or inert ingredients which the term describes are suitable for use in contact with the tissues of humans and lower animals without undue toxicity, incompatibility, instability, irritation, allergic response, and the like, commensurate with a reasonable benefit/risk ratio.

Typically, the pharmaceutically-acceptable oral cleaning carrier components of the oral cleaning components of the oral cleaning compositions will generally comprise from about 50% to about 99.99%, preferably from about 65% to about 99.99%, more preferably from about 65% to about 99%, by weight of the composition.

The pharmaceutically-acceptable carrier components and optional components which may be included in the oral cleaning compositions of the present invention are well known to those skilled in the art. A wide variety of composition types, carrier components and optional components useful in the oral cleaning compositions are disclosed in the references cited hereinabove.

In another embodiment of the present invention, denture cleaning compositions for cleaning dentures outside of the oral cavity comprise one or more protease conjugates of the present invention. Such denture cleaning compositions comprise an effective amount of one or more of the protease conjugates, preferably from about 0.0001% to about 50%, more preferably from about 0.001% to about 35%, more preferably still from about 0.01% to about 20%, by weight of the composition, and a denture cleansing carrier. Various denture cleansing composition formats such as effervescent tablets and the like are well known in the art (see. e.g., U.S. Pat. No. 5,055,305, Young), and are generally appropriate for incorporation of one or more of the protease conjugates for removing proteinaceous stains from dentures.

In another embodiment of the present invention, contact lens cleaning compositions comprise one or more protease conjugates of the present invention. Such contact lens cleaning compositions comprise an effective amount of one or more of the protease conjugates, preferably from about 0.01% to about 50% of one or more of the protease conjugates, more preferably from about 0.01% to about 20%, more preferably still from about 1% to about 5%, by weight of the composition, and a contact lens cleaning carrier. Various contact lens cleaning composition formats such as tablets, liquids, and the like are well known in the art and are generally appropriate for incorporation of one or more protease conjugates of the present invention for removing proteinaceous stains from contact lens.

EXAMPLES 20–23

Contact Lens Cleaning Solution

|  | Ex. 20 | Ex. 21 | Ex. 22 | Ex. 23 |
|---|---|---|---|---|
| Protease Conjugate of Example 5 | 0.01% | 0.5% | 0.1% | 2.0% |
| Glucose | 50.0% | 50.0% | 50.0% | 50.0% |
| Nonionic surfactant (polyoxyethlene-polyoxypropylene copolymer) | 2.0% | 2.0% | 2.0% | 2.0% |
| Anionic surfactant (polyoxyethylene-alkylphenylether sodium sulfricester) | 1.0% | 1.0% | 1.0% | 1.0% |
| Sodium Chloride | 1.0% | 1.0% | 1.0% | 1.0% |
| Borax | 0.30% | 0.30% | 0.30% | 0.30% |
| Water | 45.69% | 45.20% | 45.60% | 43.70% |

EXAMPLES 24–27

Bodywash Products

|  | Ex. 24 | Ex. 25 | Ex. 26 | Ex. 27 |
|---|---|---|---|---|
| Water | 62.62% | 65.72% | 57.72% | 60.72% |
| Disodium EDTA | 0.2% | 0.2% | 0.2% | 0.2% |
| Glycerine | 3.0% | 3.0% | 3.0% | 3.0% |
| Polyquaternium 10 | 0.4% | 0.4% | 0.4% | 0.4% |
| Sodium laureth sulphate | 12.0% | 12.0% | 12.0% | 12.0% |
| Cocamide MEA | 2.8% | 2.8% | 2.8% | 2.8% |
| Sodium lauraphoacetate | 6.0% | 6.0% | 6.0% | 6.0% |
| Myristic Acid | 1.6% | 1.6% | 1.6% | 1.6% |
| Magnesium sulphate heptahydrate | 0.3% | 0.3% | 0.3% | 0.3% |
| Trihydroxystearin | 0.5% | 0.5% | 0.5% | 0.5% |
| PEG-6 caprylic/capric triglycerides | 3.0% | — | — | — |
| Sucrose polyesters of cottonate fatty acid | 3.0% | — | — | — |
| Sucrose polyesters of behenate fatty acid | 3.0% | — | 4.0% | — |
| Petrolatum | — | 4.0% | 8.0% | — |
| Mineral Oil | — | — | — | 6.0% |
| DMDM Hydantoin | 0.08% | 0.08% | 0.08% | 0.08% |
| Protease Conjugate of Example 6 | 0.1% | 2.0% | 2.0% | 5.0% |
| Citric Acid | 1.40% | 1.40% | 1.40% | 1.40% |

EXAMPLES 28–31

Facewash Products

|  | Ex.28 | Ex.29 | Ex.30 | Ex.31 |
|---|---|---|---|---|
| Water | 66.52% | 65.17% | 68.47% | 68.72% |
| Disodium EDTA | 0.1% | 0.1% | 0.2% | 0.2% |
| Citric Acid | — | — | 1.4% | 1.4% |
| Sodium Laureth-3 Sulfate | 3.0% | 3.5% | — | — |

Facewash Products

| | Ex.28 | Ex.29 | Ex.30 | Ex.31 |
|---|---|---|---|---|
| Sodium Laureth-4 Carboxylate | 3.0% | 3.5% | — | — |
| Laureth-12 | 1.0% | 1.2% | — | — |
| Polyquaternium 10 | — | — | 0.4% | 0.4% |
| Polyquaternium 25 | 0.3% | 0.3% | — | — |
| Glycerine | 3.0% | 3.0% | 3.0% | 3.0% |
| Sodium Lauroamphoacetate | — | — | 6.0% | 6.0% |
| Lauric Acid | 6.0% | 6.0% | 3.0% | 3.0% |
| Myristic Acid | — | — | 3.0% | 3.0% |
| Magnesium sulphate heptahydrate | 2.3% | 2.0% | 2.0% | 2.0% |
| Triethanol amine | 4.0% | 4.0% | 4.0% | 4.0% |
| Trihydroxystearin | 0.5% | 0.5% | 0.5% | 0.5% |
| Sucrose polyesters of behenate fatty acid | 2.0% | 2.0% | — | — |
| Sucrose polyesters of cottonate fatty acid | 3.0% | 2.0% | — | — |
| PEG-6 caprylic/capric triglycerides | — | — | — | 2.0% |
| Petrolatum | — | — | 4.0% | — |
| Mineral Oil | — | — | — | 2.0% |
| Cocamidopropyl betaine | 2.0% | 3.0% | 1.8% | 1.8% |
| Lauryl dimethylamine oxide | 1.0% | 1.2% | 1.2% | 1.2% |
| Dex Panthenol | 1.0% | 0.25% | 0.25% | — |
| DMDM Hydantoin | 0.08% | 0.08% | 0.08% | 0.08% |
| Protease Conjugate of Example 2 | 1.0% | 2.0% | 0.5% | 0.5% |
| Fragrance | 0.2% | 0.2% | 0.2% | 0.2% |

EXAMPLES 32–33

Leave-on Skin Moisturizing Composition

| | Ex. 32 | Ex. 33 |
|---|---|---|
| Glycerine | 5.0% | — |
| Stearic acid | 3.0% | — |
| $C_{11-13}$ Isoparaffin | 2.0% | — |
| Glycol stearate | 1.5% | — |
| Propylene glycol | — | 3.0% |
| Mineral oil | 1.0% | 10.0% |
| Sesame oil | — | 7.0% |
| Petrolatum | — | 1.8% |
| Triethanolamine | 0.7% | — |
| Cetyl acetate | 0.65% | — |
| Glyceryl stearate | 0.48% | 2.0% |
| TEA stearate | — | 2.5% |
| Cetyl alcohol | 0.47% | — |
| Lanolin alcohol | — | 1.8% |
| DEA - cetyl phosphate | 0.25% | — |
| Methylparaben | 0.2% | 0.2% |
| Propylparaben | 0.12% | 0.1% |
| Carbomer 934 | 0.11% | — |
| Disodium EDTA | 0.1% | — |
| Protease Conjugate of Example 4 | 0.1% | 0.5% |
| Water | 84.32% | 71.1% |

EXAMPLE 34

Cleansing Wipe Composition

| | |
|---|---|
| Propylene Glycol | 1.0% |
| Ammonium lauryl sulfate | 0.6% |
| Succinic acid | 4.0% |
| Sodium succinate | 3.2% |
| Triclosan ® | 0.15% |
| Protease Conjugate of Example I | 0.05% |
| Water | 91.0% |

The above composition is impregnated onto a woven absorbent sheet comprised of cellulose and/or polyester at avout 250%, by weight of the absorbent sheet.

---

What is claimed is:

1. A protease conjugate comprising a protease moiety and one or more addition moieties wherein each addition moiety is covalently attached to an amino acid of the protease moiety at a clip site protection position selected from the group of positions corresponding to positions consisting of 160, 161, and 261, of the amino acid sequence of subtilisin BPN' set forth in SEQ ID NO:1.

2. A protease conjugate according to claim 1 wherein each addition moiety, independently, has the structure:

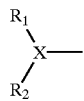

wherein X is selected from the group consisting of nil and a linking moiety; $R_1$ is selected from the group consisting of nil, a first polypeptide, and a first polymer; and $R_2$ is selected from the group consisting of nil, a second polypeptide, and a second polymer; wherein at least one of X, $R_1$, and $R_2$ is not nil.

3. A protease conjugate according to claim 2 wherein the protease moiety has a modified amino acid sequence of a parent amino acid sequence, wherein the modified amino acid comprises a substitution by a substituting amino acid at one or more clip site protection positions selected from the group consisting of 160, 161, and 261, wherein each addition moiety is covalently attached to one of the substituting amino acids.

4. A protease conjugate according to claim 3 wherein the substituting amino acid is cysteine.

5. A protease conjugate according to claim 4 wherein the parent amino acid sequence is selected from the group consisting of subtilisin BPN', subtilisin Carlsberg, subtilisin DY, subtilisin 309, proteinase K, thermitase, Protease A, Protease B, Protease C, and Protease D.

6. A protease conjugate according to claim 5 wherein clip site protection positions are selected from the group consisting of 160, 161, and 261.

7. A protease conjugate according to claim 6 wherein clip site protection positions are selected from the group consisting of 160, 161, and 261.

8. A protease conjugate according to claim 7 wherein clip site protection positions are selected from the group consisting of 160, 161, and 261.

9. A protease conjugate according to claim 8 wherein clip site protection positions are selected from the group consisting of 160, 161, and 261.

10. A protease conjugate according to claim 9 wherein $R_2$ is nil.

11. A protease conjugate according to claim 10 wherein $R_1$ is nil.

12. A protease conjugate according to claim 9 wherein $R_1$ is the first polymer and $R_2$ is selected from the group consisting of nil and the second polymer.

13. A protease conjugate according to claim 12 wherein $R_2$ is nil and the first polymer is a polyethylene glycol.

14. A protease conjugate according to claim 13 wherein the clip site protection positions selected from the group consisting of 160, 161, and 261.

15. A protease conjugate according to claim 14 wherein the clip site protection positions selected from the group consisting of 160, 161, and 261.

16. A protease conjugate according to claim 15 wherein the clip site protection positions selected from the group consisting of 160, 161, and 261.

17. A protease conjugate according to claim 1 additionally comprising one or more supplementary moieties selected from the group consisting of small molecules, polypeptides, and polymers.

18. A cleaning composition comprising a protease conjugate according to claim 1 and a cleaning composition carrier.

19. A personal care composition comprising a protease conjugate according to claim 1 and a personal care carrier.

* * * * *

UNITED STATES PATENT AND TRADEMARK OFFICE
CERTIFICATE OF CORRECTION

PATENT NO. : 6,566,115 B1 Page 1 of 1
DATED : May 20, 2003
INVENTOR(S) : Weisgerber et al.

It is certified that error appears in the above-identified patent and that said Letters Patent is hereby corrected as shown below:

Column 5,
Lines 20 and 30, "Try104" should read -- Tyr104 --.

Column 10,
Line 41, "480-4815" should read -- 4807-4815 --.

Column 26,
Line 38, "avove" should read -- above --.

Column 28,
Lines 61, 64 and 67, "selected" should read -- are selected --.

Signed and Sealed this

Twelfth Day of August, 2003

JAMES E. ROGAN
*Director of the United States Patent and Trademark Office*